(12) United States Patent
Beruda et al.

(10) Patent No.: US 7,847,144 B2
(45) Date of Patent: Dec. 7, 2010

(54) ABSORBENT ARTICLES COMPRISING FLUID ACQUISITION ZONES WITH SUPERABSORBENT POLYMERS

(75) Inventors: Holger Beruda, Kelkheim-Ruppertshain (DE); Yasue Nakagawa, Bad Soden (DE); Andrea Lieselotte Link, Schwalbach (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/941,672

(22) Filed: Sep. 15, 2004

(65) Prior Publication Data

US 2005/0070867 A1 Mar. 31, 2005

(30) Foreign Application Priority Data

Sep. 25, 2003 (EP) ................................. 03021716

(51) Int. Cl.
*A61F 13/53* (2006.01)
*A61F 13/537* (2006.01)

(52) U.S. Cl. ....................................... 604/368; 604/378

(58) Field of Classification Search ......... 604/367–368, 604/358, 381
See application file for complete search history.

(56) References Cited

U.S. PATENT DOCUMENTS

| 3,479,310 A | 11/1969 | Dieter et al. |
|---|---|---|
| 3,661,875 A | 5/1972 | Sieja |
| 3,699,103 A | 10/1972 | Kiss |
| 3,770,731 A | 11/1973 | Jaeger |
| 3,898,143 A * | 8/1975 | Assarsson et al. ............. 522/88 |
| 3,905,929 A | 9/1975 | Noll |
| 3,929,678 A | 12/1975 | Laughlin et al. |
| 4,062,817 A | 12/1977 | Westerman |
| 4,076,663 A | 2/1978 | Masuda et al. |
| 4,092,286 A | 5/1978 | Noll et al. |
| 4,093,776 A | 6/1978 | Aoki et al. |
| 4,156,664 A | 5/1979 | Skinner et al. |
| 4,190,566 A | 2/1980 | Noll et al. |
| 4,340,706 A | 7/1982 | Obayashi et al. |

(Continued)

FOREIGN PATENT DOCUMENTS

AU 2002-21743 B2 5/2002

(Continued)

OTHER PUBLICATIONS

Co-pending U.S. Appl. No. 10/950,011 (US-2005/0101928A1), (Notice of Allowance Received Mar. 25, 2008; issue fee paid Jun. 24, 2008).

(Continued)

*Primary Examiner*—Tatyana Zalukaeva
*Assistant Examiner*—Paula L Craig
(74) *Attorney, Agent, or Firm*—Amy M. Foust; William E. Gallagher; Richard L. Alexander

(57) ABSTRACT

The present invention relates to absorbent articles comprising superabsorbent polymer particles especially suitable for use in the fluid acquisition zone of the absorbent core. The superabsorbent polymer particles are coated with cationic polymers having 1 to 25 mol/kg, referring to the total weight of the cationic polymers, of cationic groups, which can be protonated. The cationic polymers are not substantially covalently bound to the superabsorbent polymer particles.

9 Claims, 2 Drawing Sheets

U.S. PATENT DOCUMENTS

| | | | |
|---|---|---|---|
| 4,392,908 A | 7/1983 | Dehnel | |
| 4,421,602 A | 12/1983 | Brunnmueller et al. | |
| 4,506,052 A | 3/1985 | Furukawa et al. | |
| 4,541,871 A | 9/1985 | Obayashi et al. | |
| 4,587,308 A | 5/1986 | Makita et al. | |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,673,402 A | 6/1987 | Weisman et al. | |
| 4,734,445 A | 3/1988 | Noda et al. | |
| 4,734,478 A | 3/1988 | Tsubakimoto et al. | |
| RE32,649 E | 4/1988 | Brandt et al. | |
| 4,735,987 A | 4/1988 | Morita et al. | |
| 4,785,030 A | 11/1988 | Noda et al. | |
| 4,789,861 A | 12/1988 | Baggett et al. | |
| 4,824,901 A | 4/1989 | Alexander et al. | |
| 4,834,735 A | 5/1989 | Alemany et al. | |
| 4,835,211 A | 5/1989 | Noda et al. | |
| 4,935,022 A | 6/1990 | Lash et al. | |
| 5,002,986 A * | 3/1991 | Fujiura et al. | 524/47 |
| 5,061,424 A | 10/1991 | Karimi et al. | |
| 5,066,745 A | 11/1991 | Engelhardt et al. | |
| 5,140,076 A | 8/1992 | Hatsuda et al. | |
| 5,147,343 A | 9/1992 | Kellenberger | |
| 5,164,459 A | 11/1992 | Kimura et al. | |
| 5,211,985 A | 5/1993 | Shirley, Jr. et al. | |
| 5,247,068 A | 9/1993 | Donachy et al. | |
| 5,281,683 A | 1/1994 | Yano et al. | |
| 5,300,054 A * | 4/1994 | Feist et al. | 604/378 |
| 5,300,565 A | 4/1994 | Berg et al. | |
| 5,331,059 A | 7/1994 | Engelhardt et al. | |
| 5,382,610 A | 1/1995 | Harada et al. | |
| 5,409,771 A | 4/1995 | Dahmen et al. | |
| 5,415,643 A | 5/1995 | Kolb | |
| 5,453,323 A | 9/1995 | Chambers et al. | |
| 5,458,592 A | 10/1995 | Abuto et al. | |
| 5,470,964 A | 11/1995 | Qin | |
| 5,525,407 A * | 6/1996 | Yang | 428/218 |
| 5,532,323 A | 7/1996 | Yano et al. | |
| 5,562,646 A | 10/1996 | Goldman et al. | |
| 5,574,121 A | 11/1996 | Irie et al. | |
| 5,576,282 A | 11/1996 | Miracle et al. | |
| 5,599,335 A | 2/1997 | Goldman et al. | |
| 5,607,759 A * | 3/1997 | Hansen et al. | 442/417 |
| 5,624,967 A | 4/1997 | Hitomi et al. | |
| 5,624,971 A | 4/1997 | Wilson | |
| 5,633,316 A | 5/1997 | Gartner et al. | |
| 5,669,894 A | 9/1997 | Goldman et al. | |
| 5,700,867 A | 12/1997 | Ishiyama et al. | |
| 5,707,950 A | 1/1998 | Kasturi et al. | |
| 5,714,156 A | 2/1998 | Schmidt et al. | |
| 5,716,703 A | 2/1998 | Payne | |
| 5,716,707 A | 2/1998 | Mukaida et al. | |
| 5,728,742 A | 3/1998 | Staples et al. | |
| 5,731,365 A | 3/1998 | Engelhardt et al. | |
| 5,762,641 A | 6/1998 | Bewick-Sonntag et al. | |
| 5,830,202 A * | 11/1998 | Bogdanski et al. | 604/378 |
| 5,836,929 A | 11/1998 | Plischke et al. | |
| 5,837,789 A | 11/1998 | Stockhausen et al. | |
| 5,840,321 A | 11/1998 | Engelhardt et al. | |
| 5,840,329 A | 11/1998 | Bai | |
| 5,843,575 A | 12/1998 | Wang et al. | |
| 5,849,405 A | 12/1998 | Wang et al. | |
| 5,849,816 A | 12/1998 | Suskind et al. | |
| 5,851,672 A * | 12/1998 | Wang et al. | 428/407 |
| 5,858,535 A | 1/1999 | Rezai et al. | |
| 5,865,824 A * | 2/1999 | Chen et al. | 604/378 |
| 5,941,862 A * | 8/1999 | Haynes et al. | 604/368 |
| 5,981,689 A * | 11/1999 | Mitchell et al. | 528/229 |
| 5,985,432 A | 11/1999 | Wang et al. | |
| 6,011,196 A | 1/2000 | Wang et al. | |
| 6,040,251 A | 3/2000 | Caldwell | |
| 6,083,210 A | 7/2000 | Young et al. | |
| 6,143,821 A | 11/2000 | Houben | |
| 6,150,469 A | 11/2000 | Harada et al. | |
| 6,222,091 B1 * | 4/2001 | Beihoffer et al. | 604/368 |
| 6,239,230 B1 | 5/2001 | Mitchell et al. | |
| 6,241,928 B1 | 6/2001 | Hatsuda et al. | |
| 6,245,051 B1 | 6/2001 | Zenker | |
| 6,258,996 B1 * | 7/2001 | Goldman | 604/368 |
| 6,265,488 B1 | 7/2001 | Fujino et al. | |
| 6,300,423 B1 | 10/2001 | Engelhardt et al. | |
| 6,359,129 B1 | 3/2002 | Hanson et al. | |
| 6,376,011 B1 | 4/2002 | Reeves et al. | |
| 6,376,618 B1 | 4/2002 | Mitchell et al. | |
| 6,380,456 B1 | 4/2002 | Goldman | |
| 6,383,960 B1 * | 5/2002 | Everett et al. | 442/394 |
| 6,387,495 B1 | 5/2002 | Reeves et al. | |
| 6,391,451 B1 | 5/2002 | Mitchell et al. | |
| 6,423,883 B1 * | 7/2002 | Morman et al. | 604/368 |
| 6,472,478 B1 | 10/2002 | Funk et al. | |
| 6,482,344 B1 | 11/2002 | Messner et al. | |
| 6,503,979 B1 | 1/2003 | Funk et al. | |
| 6,534,572 B1 | 3/2003 | Ahmed et al. | |
| 6,559,239 B1 | 5/2003 | Riegel et al. | |
| 6,562,743 B1 * | 5/2003 | Cook et al. | 442/409 |
| 6,657,015 B1 | 12/2003 | Riegel et al. | |
| 6,710,141 B1 | 3/2004 | Heide et al. | |
| 6,730,387 B2 | 5/2004 | Rezai et al. | |
| 6,808,801 B2 | 10/2004 | George et al. | |
| 6,809,158 B2 | 10/2004 | Ikeuchi et al. | |
| 6,822,135 B2 | 11/2004 | Soerens et al. | |
| 6,849,665 B2 | 2/2005 | Frenz et al. | |
| 6,906,131 B2 | 6/2005 | Ahmed et al. | |
| 6,911,499 B1 | 6/2005 | Brehm et al. | |
| 6,979,564 B2 | 12/2005 | Glucksmann et al. | |
| 7,049,000 B2 | 5/2006 | Schmidt et al. | |
| 7,175,910 B2 | 2/2007 | Ehrnsperger et al. | |
| 7,183,360 B2 | 2/2007 | Daniel et al. | |
| 7,183,456 B2 | 2/2007 | Hatsuda et al. | |
| 7,199,211 B2 | 4/2007 | Popp et al. | |
| 7,235,708 B2 * | 6/2007 | Guidotti et al. | 604/369 |
| 7,250,481 B2 | 7/2007 | Jaworek et al. | |
| 7,259,212 B2 | 8/2007 | Popp et al. | |
| 7,311,968 B2 | 12/2007 | Ehrnsperger et al. | |
| 7,396,584 B2 | 7/2008 | Azad et al. | |
| 7,405,321 B2 | 7/2008 | Riegel et al. | |
| 7,405,341 B2 * | 7/2008 | Beruda et al. | 604/368 |
| 7,420,013 B2 | 9/2008 | Riegel et al. | |
| 2002/0019187 A1 | 2/2002 | Carroll et al. | |
| 2002/0128618 A1 | 9/2002 | Frenz et al. | |
| 2002/0150761 A1 * | 10/2002 | Lange et al. | 428/407 |
| 2002/0165288 A1 | 11/2002 | Frenz et al. | |
| 2003/0069359 A1 * | 4/2003 | Torii et al. | 525/178 |
| 2003/0105442 A1 * | 6/2003 | Johnston et al. | 604/368 |
| 2003/0135177 A1 * | 7/2003 | Baker | 604/368 |
| 2003/0148684 A1 | 8/2003 | Cramer et al. | |
| 2003/0195293 A1 | 10/2003 | Lubnin | |
| 2004/0024092 A1 | 2/2004 | Soerens et al. | 524/13 |
| 2004/0025836 A1 | 2/2004 | Almkvist et al. | |
| 2004/0039360 A1 * | 2/2004 | Ehrnsperger et al. | 604/368 |
| 2004/0097895 A1 | 5/2004 | Busam et al. | |
| 2004/0122390 A1 * | 6/2004 | Soerens et al. | 604/367 |
| 2004/0162536 A1 | 8/2004 | Becker | |
| 2004/0180998 A1 | 9/2004 | Gonzales et al. | |
| 2004/0214499 A1 * | 10/2004 | Qin et al. | 442/414 |
| 2004/0214937 A1 | 10/2004 | Miller | |
| 2005/0008839 A1 | 1/2005 | Cramer et al. | |
| 2005/0013992 A1 * | 1/2005 | Azad et al. | 428/327 |
| 2005/0031852 A1 | 2/2005 | Schmidt et al. | |
| 2005/0031868 A1 | 2/2005 | Schmidt et al. | |
| 2005/0031872 A1 | 2/2005 | Schmidt et al. | |
| 2005/0033225 A1 | 2/2005 | Wu et al. | |
| 2005/0033255 A1 | 2/2005 | Fossum et al. | |

| | | | |
|---|---|---|---|
| 2005/0033256 A1 | 2/2005 | Schmidt et al. | |
| 2005/0043467 A1 | 2/2005 | Bruchmann et al. | |
| 2005/0043474 A1 | 2/2005 | Schmidt et al. | |
| 2005/0065237 A1 | 3/2005 | Schmidt et al. | |
| 2005/0070867 A1 | 3/2005 | Beruda et al. | |
| 2005/0096435 A1 | 5/2005 | Smith et al. | |
| 2005/0165208 A1 | 7/2005 | Popp et al. | |
| 2005/0176910 A1 | 8/2005 | Jaworek et al. | |
| 2005/0215752 A1 | 9/2005 | Popp et al. | |
| 2005/0245684 A1 | 11/2005 | Daniel et al. | |
| 2006/0004336 A1 | 1/2006 | Zhang et al. | |
| 2006/0020078 A1 | 1/2006 | Popp et al. | |
| 2006/0040579 A1 | 2/2006 | Sheldon et al. | |
| 2006/0069367 A1 * | 3/2006 | Waksmundzki et al. | 604/378 |
| 2006/0155057 A1 | 7/2006 | Hermeling et al. | |
| 2006/0167215 A1 | 7/2006 | Hermeling et al. | |
| 2006/0211828 A1 | 9/2006 | Daniel et al. | |
| 2006/0212011 A1 | 9/2006 | Popp et al. | |
| 2006/0235141 A1 | 10/2006 | Riegel et al. | |
| 2006/0247377 A1 | 11/2006 | Riegel et al. | |
| 2007/0027435 A1 * | 2/2007 | Nakagawa et al. | 604/368 |
| 2007/0160539 A1 | 7/2007 | Friedman et al. | |
| 2007/0203289 A1 | 8/2007 | Bruchmann et al. | |

FOREIGN PATENT DOCUMENTS

| | | |
|---|---|---|
| CA | 2 433 044 A1 | 2/2002 |
| DE | 2 239 074 | 2/1973 |
| DE | 2 730 514 A1 | 1/1979 |
| DE | 4 020 780 | 8/1991 |
| DE | 4020780 C1 | 8/1991 |
| DE | 10 204 937 A | 8/2003 |
| DE | 10 355 401 A1 | 6/2005 |
| EP | 0 300 571 | 1/1989 |
| EP | 0493011 A2 | 7/1992 |
| EP | 0 509 708 | 10/1992 |
| EP | 0509708 A1 | 10/1992 |
| EP | 0 612 533 A | 8/1994 |
| EP | 0 618 005 | 10/1994 |
| EP | 0 686 650 A1 | 12/1995 |
| EP | 0 689 817 A2 | 1/1996 |
| EP | 0 691 133 A | 1/1996 |
| EP | 0 695 763 A | 2/1996 |
| EP | 0 705 643 | 4/1996 |
| EP | 0 799 258 B1 | 10/1997 |
| EP | 631768 B1 | 4/1998 |
| EP | 0 900 571 A | 3/1999 |
| EP | 0 640 330 B1 | 5/2000 |
| EP | 1 013 291 A | 6/2000 |
| EP | 752892 B1 | 7/2001 |
| EP | 1 403 419 A1 | 3/2004 |
| JP | 56-158232 | 12/1981 |
| JP | 56-159232 * | 12/1981 |
| JP | 57-168921 A | 10/1982 |
| JP | 60-135432 A | 7/1985 |
| JP | 2002-242858 A | 9/1990 |
| JP | 07-82630 | 3/1995 |
| JP | 2009-031203 A | 2/1997 |
| JP | 2000-198858 A | 7/2000 |
| WO | WO 9008789 A1 | 8/1990 |
| WO | WO 90/15830 A1 | 12/1990 |
| WO | WO 9216565 A1 | 10/1992 |
| WO | WO 9305080 A1 | 3/1993 |
| WO | WO 93/21237 A1 | 10/1993 |
| WO | WO 96/14885 A1 | 5/1996 |
| WO | WO-97/12575 A1 | 4/1997 |
| WO | WO 99/47072 A | 9/1999 |
| WO | WO 01/45758 A1 | 6/2001 |
| WO | WO 01/54641 A1 | 8/2001 |
| WO | WO 03043670 A1 | 5/2003 |
| WO | WO 03/051417 A | 6/2003 |
| WO | WO 03/053298 A | 7/2003 |
| WO | WO 03/057964 A | 7/2003 |
| WO | WO 03/064753 A1 | 8/2003 |
| WO | WO 03/064754 A1 | 8/2003 |
| WO | WO 2004/028575 A1 | 4/2004 |
| WO | WO 2004/071340 A2 | 8/2004 |
| WO | WO 2004/071341 A2 | 8/2004 |
| WO | WO 2004/071342 A2 | 8/2004 |
| WO | WO 2005/014065 A | 2/2005 |
| WO | WO 2005/014067 A1 | 2/2005 |
| WO | WO 2005/014697 A1 | 2/2005 |
| WO | WO 2006/042704 A | 4/2006 |

OTHER PUBLICATIONS

All Office Actions issued in co-pending U.S. Appl. No. 10/950,011 (US-2005/0101928A1).

* cited by examiner

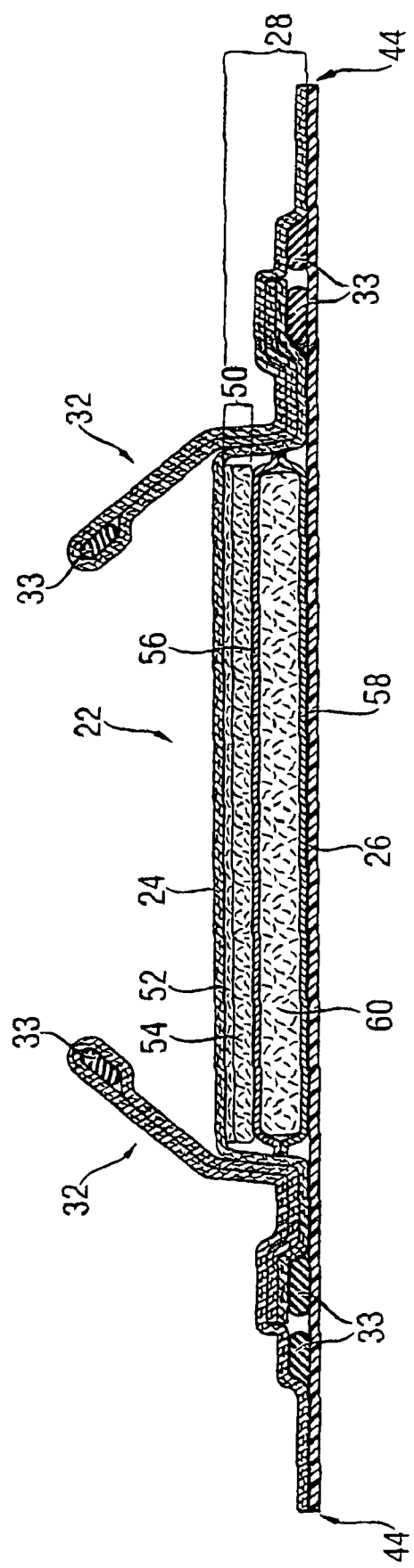

ABSORBENT ARTICLES COMPRISING FLUID ACQUISITION ZONES WITH SUPERABSORBENT POLYMERS

This application claims priority to European Application No. 03021716.0 filed Sep. 25, 2003.

FIELD OF THE INVENTION

The present invention relates to absorbent articles, which are intended to receive and retain bodily discharges such as urine. Such articles include disposable hygiene articles such as baby diapers, training pants, adult incontinence articles, feminine care articles and the like. To provide absorbent articles with thinner and dryer absorbent cores only became possible with the development of new highly absorbent gel materials able to acquire and store liquids. A second aspect is the ability to maintain the comfort and performance of such high super absorbent polymer concentration articles during the full usage cycle of the article, from dry to fully loaded, especially by improving the ability of the cores to withstand the forces experienced by such articles during use. This ability to remain intact is also often referred to as 'wet integrity' of the core.

The development and improvement of highly absorbent gel materials so far mainly focused on applications of these materials in the fluid storage zone of the absorbent core. In contrast thereto, the highly absorbent gel materials of the present invention are especially suitable for use in the fluid acquisition zone of the absorbent core.

BACKGROUND OF THE INVENTION

Absorbent articles for receiving and retaining bodily discharges (e.g., urine or faeces) such as disposable diapers, training pants, and adult incontinence articles are well known in the art, and significant effort has been spent against improving their performance. Such improvements generally aim at addressing the primary function of such articles, namely retaining body fluids, but also at minimizing the negatives associated with wearing such articles by increasing the comfort of the wearer.

Many improvements are related to the "absorbent core" of the absorbent article. In the absorbent core the waste material is acquired by the article (picked up), then conducted away from the location of acquisition (distributed), and then stored (retained).

It is well established that reducing the thickness of the article by reducing the thickness of the absorbent core, helps to improve comfort. This, however, was always a question of balance between liquid handling performance and thickness. Also a substantial amount of cushioning was considered necessary for comfortable diapers. Finally the skilled person considered it impossible to reduce or even remove the fibrous material commonly applied in absorbent cores to a point where the modern particulate super absorbent materials would take over the biggest part or even all of the liquid acquisition and distribution functionalities previously provided by fibrous matrixes. Even if there were structures which could possibly provide all such beneficial aspects when dry, it was completely inconceivable that this could be built into an absorbent core such that the liquid handling and comfort performance would be maintained even after the first gushes of liquid had been absorbed.

The development of absorbent cores of particular thinness has beneficial aspects, which make such a development the subject of substantial commercial interest. For example, thinner diapers are not just less bulky to wear, conform better to the body and fit better under clothing, they are also more compact in the package, making the diapers easier for the consumer to carry and store. Compactness in packaging also results in reduced distribution costs for the manufacturer and distributor, including less shelf space required in the store per diaper unit.

As indicated, the ability to provide thinner absorbent articles such as diapers has been dependent on the ability to develop relatively thin absorbent cores that can acquire and store large quantities of discharged body fluids, in particular urine. In this regard, the use of absorbent polymers often referred to as "hydrogels," "super absorbents" or "hydrocolloid" material has been particularly important. See, for example, U.S. Pat. No. 3,699,103 and U.S. Pat. No. 3,770,731, that disclose the use of such absorbent polymers (hereafter referred to as any of the following: hydrogel forming absorbent polymers, super absorbents, super absorbent polymers or SAPs, absorbent gel materials or AGMs). Indeed, the development of thinner diapers has been the direct consequence of thinner absorbent cores that take advantage of the ability of these SAPs to absorb large quantities of discharged body fluids, typically when used in combination with a fibrous matrix. See, for example, U.S. Pat. No. 4,673,402 and U.S. Pat. No. 4,935,022, that disclose dual-layer core structures comprising a fibrous matrix and SAPs useful in fashioning thin, compact, non-bulky diapers.

SAPs are often made by initially polymerizing unsaturated carboxylic acids or derivatives thereof, such as acrylic acid, alkali metal (e.g., sodium and/or potassium) or ammonium salts of acrylic acid, alkyl acrylates, and the like. These polymers are rendered water-insoluble, yet water-swellable, by slightly and homogeneously cross-linking the carboxyl group-containing polymer chains with conventional di- or poly-functional monomer materials, such as N,N'-methylene-bisacryl-amide, trimethylol-propane-triacrylate or trial-lyl-amine. These slightly cross-linked absorbent polymers still comprise a multiplicity of anionic (charged) carboxyl groups attached to the polymer backbone. It is these charged carboxyl groups that enable the polymer to absorb body fluids as the result of osmotic forces, thus forming hydrogels.

It is often desirable to increase the stiffness of SAP particles. Typically, this is done by surface cross-linking, wherein the carboxyl-groups exposed on the surface of the SAP particles are additionally cross-linked to each other. Other methods to increase the stiffness comprise coating the SAP particles. Such coatings are known for example from WO 97/12575, which discloses absorbent materials comprising absorbent gelling particles and a polycationic polymer covalently bonded to the absorbent gelling particles. European patent application EP 493 011 A2 refers to an absorbent matter comprising a water-absorbent resin particle having an acidic group on the surface, a cellulose fiber and a cationic high-molecular compound having a weight-average molecular weight of 2,000 or more. Further, WO 03/043670 discloses superabsorbent particles with a shell comprising cationic polymer cross-linked by the addition of cross-linker and adhered to the hydrogel-forming polymer by applying a coating solution containing both a cationic polymer and cross-linker.

However, the development and improvement of SAPs has so far mainly focused on use of the SAPs for final storage of liquid in the absorbent core. Consequently, it would be desirable to have SAPs, which are especially suitable for fluid acquisition and distribution in the fluid acquisition zone of the absorbent core. By replacing the fibers used in the fluid acquisition zone of prior art absorbent cores with SAPs, it would be possible to further reduce the bulk and thickness of the absorbent core.

A problem in developing SAPs for use in the fluid acquisition zone is that the demands on the physical and chemical properties of these SAPs differ considerably from the requirements for use in the fluid storage zone. For example, it is desirable that SAPs in the fluid acquisition zone are able to quickly acquire via capillary pressure and temporarily hold fluids in voids between the SAP particles, especially in "gush" situations. The focus is not primarily on SAPs with high capacity, but it is important that a hydrogel-bed formed from SAPs has high porosity and permeability in order to be able to provide enough interstices between the swollen SAPs.

It would also be desirable to have SAP particles for use in absorbent cores, especially in the fluid acquisition zones, which have a high Free Swelling Rate (FSR). The FSR is related to the surface area of the SAP particles, and thus to their particle size, particle shape and morphology of the particles (e.g., a porous SAP particle versus a non-porous SAP particle). SAP particles having a high surface area typically also have a high FSR, which means they are able to quickly absorb liquids. The ability to quickly absorb liquids is especially important in the fluid acquisition zone of absorbent cores to create sufficient void volume. It is especially desirable to have SAP particles for use in the fluid acquisition zone, which are highly saturated already after the fist gush of liquid.

Moreover, it would be desirable to be able to provide an absorbent core comprising an acquisition zone having a relatively high concentration of SAP particles with relatively high porosities, and high permeability, and in a matrix that provides sufficient wet integrity such that its capability for acquiring and transporting fluids is not substantially reduced or minimized, even when subjected to normal use forces.

It would also be highly desirable to be able to use SAPs in these absorbent cores, especially in the fluid acquisition zones, that, when swollen by body fluids, continue to have a good wet integrity and high porosity such that the void volume per unit weight of absorbent polymer relatively high and preferably is close to that of an air-laid fibrous web, such as have been used in fluid acquisition zones of prior art absorbent articles.

Hence it is an object of the present invention to provide absorbent articles having an improved fit especially by reducing their thickness but also when being loaded, together with good fluid handling performance, especially by using materials having particularly suitable fluid distribution properties when dry and during progressive saturation with liquids.

It is a further object of the invention to achieve this by using super absorbent polymers particles.

SUMMARY OF THE INVENTION

In one embodiment, the present invention relates to absorbent articles comprising a substantially liquid pervious topsheet, a substantially liquid impervious backsheet and an absorbent core between the topsheet and the backsheet. The topsheet and the backsheet are at least partially joined together. The absorbent core comprises at least one fluid acquisition zone wherein the fluid acquisition zone comprises superabsorbent polymer particles, characterized in that:

a) the superabsorbent polymer particles further are surface coated with cationic polymers, wherein the cationic polymers have 1 to 25 mol/kg, referring to the total weight of the cationic polymers, of cationic groups, which can be protonated, and wherein the cationic polymers are not substantially covalently bound to said superabsorbent polymer particles, and b) the superabsorbent polymer particles have a Cylinder Centrifuge Retention Capacity (CCRC) of less than 25 g/g.

An alternative embodiment of the present invention relates to absorbent articles comprising a substantially liquid pervious topsheet, a substantially liquid impervious backsheet and an absorbent core between the topsheet and the backsheet. The topsheet and the backsheet are at least partially joined together. The absorbent core comprises at least one fluid acquisition zone wherein the fluid acquisition zone comprises superabsorbent polymer particles, characterized in that:

a) the superabsorbent polymer particles further are surface coated with cationic polymers, wherein the cationic polymers have 1 to 25 mol/kg, referring to the total weight of the cationic polymers, of cationic groups, which can be protonated, and wherein the cationic polymers are not substantially covalently bound to said superabsorbent polymer particles, and b) the fluid acquisition zone comprises the superabsorbent polymer particles in a concentration of at least 50% by weight of the fluid acquisition zone.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 2 is a cross-sectional view of the disposable diaper shown in FIG. 1

DETAILED DESCRIPTION OF THE INVENTION

Figure 1:
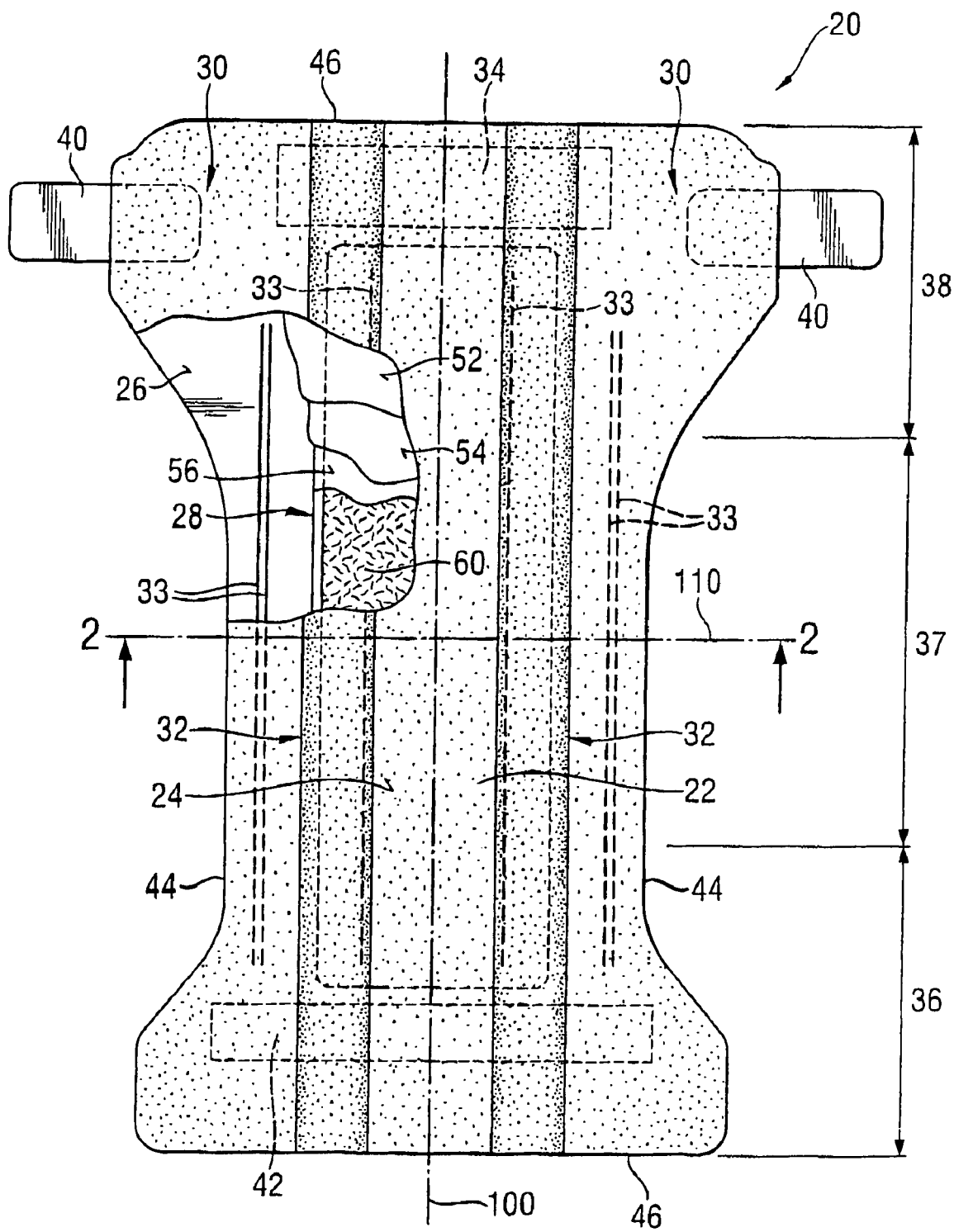
FIG. 1 is a top plan view of a disposable diaper, with the upper layers partially cut away.

As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like. Preferably, the absorbent articles of the present invention are disposable absorbent articles.

Preferred absorbent articles of the present invention are diapers. As used herein, "diaper" refers to an absorbent article generally worn by infants and incontinent persons about the lower torso.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

As used herein, the term "absorbent core" refers to a component of an absorbent article that is primarily responsible for fluid handling properties of the article, including acquiring, transporting, distributing and storing body fluids. As such, the absorbent core typically does not include the topsheet or backsheet of the absorbent article.

The absorbent core of the present invention comprises at least one fluid acquisition zone and at least one fluid storage zone. The fluid acquisition zone and the fluid storage zone may be portions or sections of an absorbent core.

The absorbent core may comprise two or more layers, wherein the fluid acquisition zone may comprise at least one layer and the fluid storage zone may comprise at least one layer.

The fluid acquisition zone is directed towards the wearer and the fluid storage zone is directed towards the garment, while the absorbent article is in use.

As used herein, the term "comprising" means that e.g., various components, zones, layers, steps and the like can be conjointly employed according to the present invention. Accordingly, the term "comprising" encompasses the more restrictive terms "made of" and "consisting of," these latter, more restrictive terms having their standard meaning as understood in the art.

The present invention relates to absorbent cores useful in the provision of absorbent incontinence articles such as baby diapers or adult incontinence articles, which articles preferably comprise a topsheet, a backsheet and an absorbent core sandwiched between the topsheet and the backsheet.

The absorbent cores of the present invention are especially useful for collection of bodily liquids such as urine. Such cores comprise super absorbent polymers (SAP), which are in the form of particles (SAP particles).

Preferably, the SAP particles are present in the fluid acquisition zone of the absorbent core in a concentration of at least 50% by weight of the fluid acquisition zone, more preferably in a concentration of at least 60% by weight.

The SAP particles may be of numerous shapes. The term "particles" refers to granules, fibers, flakes, spheres, powders, platelets and other shapes and forms known to persons skilled in the art of SAPs. For example, the particles can be in the form of granules or beads, having a particle size from about 10 µm to about 1000 µm, preferably from about 100 µm to about 1000 µm, even more preferably from about 150 µm to about 850 µm and most preferably from about 150 µm to about 500 µm. In another embodiment, the SAPs can be in the shape of fibers, i.e. elongated, acicular SAP particles. In those embodiments, the SAP fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Preferred SAPs of the present invention are spherical-like particles. According to the present invention and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle.

The SAPs useful in the present invention include a variety of water-insoluble, but water-swellable polymers capable of absorbing large quantities of fluids. Such polymers materials are generally known in the art and include all those well-known polymers used or deemed useful in the context of disposable absorbent article technology. Particularly the SAPs disclosed in EP-A-752 892 or those disclosed in a textbook entitled "Modern Super Absorbent Technology" by F. L. Buchholz and A. T. Graham, published by Wiley VCH, New York, 1998 are useful in the context of the present invention.

Preferred polymer materials for use in making SAP particles are slightly network cross linked polymers of partially neutralized polyacrylic acids and starch derivatives thereof. Preferably, the SAP particles comprise from 25% to 95% by weight, more preferably from 50% to 80% by weight, neutralized, slightly network cross-linked, polyacrylic acid. Network cross-linking renders the polymer substantially water-insoluble and, in part, determines the absorptive capacity and extractable polymer content characteristics of the hydrogel-forming absorbent polymers. Processes for network cross linking these polymers and typical network cross-linking agents are described in greater detail in U.S. Pat. No. 4,076,663 or references cited supra.

While the SAP is preferably of one type (i.e., homogeneous), mixtures of polymers can also be used in the present invention. The SAPs can also comprise mixtures with low levels of one or more additives, such as for example powdered silica, surfactants, glue, binders, and the like. Furthermore, the SAPs can comprise a gradient in particle size or can comprise a certain range of particle size.

Many of the known SAPs exhibited gel blocking. "Gel blocking" occurs when particles of the SAP are wetted and the particles swell so as to inhibit fluid transmission to other zones or regions of the absorbent structure. Wetting of these other regions of the absorbent core therefore takes place via a very slow diffusion process. In practical terms, this means acquisition of fluids by the absorbent structure is much slower than the rate at which fluids are discharged, especially in gush situations. Leakage from the absorbent article can take place well before the particles of SAP in the absorbent core are even close to being fully saturated or before the fluid can diffuse or wick past the "blocking" particles into the rest of the absorbent core. Gel blocking can be a particularly acute problem if the particles of SAP do not have adequate gel strength and deform or spread under stress once the particles swell with absorbed fluid. See U.S. Pat. No. 4,834,735. The problem of gel blocking is especially critical in the present invention, because the SAP particles are preferably applied in the fluid acquisition zone. In the fluid acquisition zone, the main task of the SAP particles is not to store liquid as is the case in most prior art uses of SAP particles in absorbent articles but the main task is to ascertain that liquid can pass through the fluid acquisition zone sufficiently quickly and to temporarily store liquid, which cannot be absorbed quick enough by the fluid storage zone.

One commonly applied way to reduce gel blocking is to make the particles stiffer, which enables the SAP particles to retain their original shape thus creating or maintaining void spaces between the particles. A well-known method to increase stiffness is to covalently cross-link the carboxyl groups exposed on the surface of the SAP particles. This method is commonly referred to as surface cross-linking.

The term "surface" describes the outer-facing boundaries of the particle. For porous SAP particles, exposed internal surfaces may also belong to the surface. The term "surface cross-linked SAP particle" refers to an SAP particle having its molecular chains present in the vicinity of the particle surface cross-linked by a compound referred to as surface cross-linker. The surface cross-linker is applied to the surface of the particle. In a surface cross-linked SAP particle the level of cross-links in the vicinity of the surface of the SAP particle is generally higher than the level of cross-links in the interior of the SAP particle.

Surface cross-linkers known in the prior art are e.g., di- or polyfunctional agents that are capable of building additional cross-links between the polymer chains of the SAPs. Surface cross-linkers include, e.g., di- or polyhydric alcohols, or derivatives thereof, capable of forming di- or polyhydric alcohols. The cross-linking is based on a reaction between the functional groups comprised by the polymer, for example, an esterification reaction between a carboxyl group (comprised by the polymer) and a hydroxyl group (comprised by the surface cross-linker).

According to the present invention the SAP particles are surface coated with cationic polymers. The cationic polymers have 1 to 25 mol/kg, referring to the total weight of the cationic polymers, of cationic groups, which can be protonated. Furthermore, the cationic polymers are not substantially covalently bonded to the superabsorbent particles. Preferably, the cationic polymers have 3 to 22 mol/kg of cationic groups, which can be protonated, more preferably 3-17 mol/kg of cationic groups, which can be protonated, even more preferably 4-14 mol/kg of cationic groups, which can be protonated and most preferably 4-12 mol/kg of cationic groups, which can be protonated.

However, preferably the cationic polymers are nitrogen-containing polymers (N-polymers) having 1 to 25 mol/kg (based on the weight of the nitrogen containing polymer) nitrogen atoms, which can be protonated. More preferably, the nitrogen-containing cationic polymers have 3 to 22 mol/kg of nitrogen atoms, which can be protonated, still more preferably 3-17 mol/kg of nitrogen atoms, which can be protonated, even more preferably 4-14 mol/kg of nitrogen atoms, which can be protonated and most preferably 4-12 mol/kg of nitrogen atoms, which can be protonated.

In a preferred embodiment of the present invention, the nitrogen-containing cationic polymer is polyethyleneimine (PEI).

In another preferred embodiment of the present invention, the nitrogen-containing cationic polymer is a partially hydrolyzed polymer. If a partially hydrolyzed nitrogen-containing cationic polymer is used for the surface coating, this polymer is preferably hydrolyzed in the range of 30%-80%, more preferably in the range of 40%-70%, and most preferably in the range of 40%-60%. The degree of hydrolyzation has a major impact on the overall charge of the cationic polymer, because only the hydrolyzed groups comprised by the coating polymer are positively charged.

A detailed description of partially hydrolyzed or at least hydrolysable polyvinyl-amides and how to make them is found in DE 31,28,478. Particularly preferred are nitrogen-containing cationic polymers provided by a polymer made from a homo-polymerization of N-vinyl-form-amide (PVFA). The PVFA is at least partially hydrolyzed to polyvinyl-amine (PVAm), preferably with a hydrolysation degree of from about 30 mol % to about 80 mol %. Solutions of partially hydrolyzed polyvinyl-form-amides are available commercially, e.g., from BASF-AG, Ludwigshafen, Germany, under the trade names Lupamin™ and Luredur™. In a particular embodiment of the present invention is the coating is a partially hydrolyzed polymer of N-vinyl-alkyl-amide or N-vinyl-alkyl-imide, more preferably a partially hydrolyzed polymer of N-vinyl-formamide.

According to the present invention, nitrogen-containing cationic polymers with primary, secondary and tertiary amines are preferred.

The cationic polymers preferably are added on the SAP particles in an amount of less than 10% by weight of said SAP particles, more preferably between 0.05% and 5% and even more preferably between 0.1% and 1.0% by weight of the SAP particles without cationic polymers (uncoated SAP particles).

Without wishing to be bound by this theory, it is believed that the cationic polymers adhere to the surface of the SAP particles via ionic bonds, Van-der-Waals forces and hydrogen bonds.

Preferably, the cationic polymers of the present invention have a weight-average molecular weight in the range of about 10,000 to about 1,000,000, more preferably in the range of about 10,000 to about 800,000 and even more preferred in the range of about 50,000 to about 750,000.

Physical Properties of the SAP Particles

1. Permeability

Permeability (also called liquid flow conductivity) is an important property of the coated SAP particles of present invention. Permeability of the SAP particles is determined based on a modification of the method to determine SFC (Saline Flow Conductivity). SFC measures the ability of a material to transport saline fluids, e.g., the ability of a hydrogel layer formed from the swollen SAP to transport body fluids under usage pressures. The method to determine SFC is described in EP-B-0 752 892, paragraph 224 and following.

For the permeability measurement of hydrogel-layer formed by SAP particles of the current invention, 0.9% Saline solution (9.00 g NaCl in 1 liter deionised water) instead of synthetic urine (known as Jayco SyUrine or Jayco Synthetic Urine, available from Jayco Pharmaceuticals, Company Hill, Pa., USA) is used during the 60 minutes of pre-swelling the SAP particles and during the liquid flow measurement. In case of SAP that forms high permeability hydrogel-layer (i.e., fast liquid flow rate), as is the case for the SAP particles of the present invention, it is particularly necessary to increase the thickness of the hydrogel-layer formed by the SAP particles in order to maintain the fluid height of 5.0 cm above the screen attached to the bottom of the cylinder throughout the whole measurement. For this purpose, the starting sample amount of dry SAP particles need to be controlled based on the capacity (Cylinder Centrifuge Retention Capacity) of SAP particles to adjust the height of the swollen hydrogel-layer formed by SAP particles between 10 mm and 20 mm. Confining pressure of 0.3 psi (2.1 kPa) is applied during the pre-swelling and the flow measurement.

Measure caliper of empty sample holder assembly to the accuracy of 0.01 mm: $h_0$.

Weigh dry SAP particles according to the appropriate amount mentioned above to the accuracy of 0.001 g.

Transfer complete sample and evenly distribute the SAP particles on the whole are of the bottom of the sample holder.

Measure caliper of empty sample holder assembly and dry SAP particle to the accuracy of 0.01 mm: $h_1$.

Put the sample holder assembly onto a filter paper (e.g., Schleicher & Schuell, No. 596, 90 mm diameter or equivalent), submerged in a large petri-dish with 0.9% saline solution where the liquid height is at least 3.0 cm and pre-swell for 60 minutes.

After 60 minutes, remove sample holder assembly from petri-dish/Saline solution and get excess liquid to drip off.

Measure caliper of sample holder assembly and swollen SAP particles to the accuracy of 0.01 mm: $h_2$.

Transfer the sample holder assembly with samples onto the support screen and let 200 ml of 0.9% saline solution flow through the sample while adjusting the 5.0 cm hydrostatic head above the screen attached to the bottom of the cylinder.

Start permeability data acquiring for 5 minutes with a data recording intervals of 10 sec for the fast flow rate hydrogel-layer.

Let drip-off excess fluid for 30 minutes by holding the outer wall of the sample holder and to avoid hydrogel-layer formed from the SAP particles contacting any surface to let the liquid easily drip off to the reservoir.

Measure the caliper of sample holder assembly and hydrogel-layer to the accuracy of 0.01 mm: $h_3$.

Calculations of permeability values are based on the flow rate that is determined via the slope of the uptake-vs-time curve. The average of three determinations is reported.

$$(\text{Permeability}) K = \{F_g \times L_{final}\} / \{\rho \times A \times \Delta P\}$$

wherein $F_g$ is the flow rate in [g/sec] determined from the calculation of the slope of the uptake-vs-time curve, i.e. liquid amount flowing through the swollen hydrogel-layer at each 10 sec time intervals, and $L_{final}$ is the average value of the initial thickness of the SAP-layer after 60 minutes of swelling, $h_2 - h_0$ and the gel layer thickness after flow and after dripping off the excess liquid, $h_3 - h_0$ in [cm].

$$L_{final} = [(h_2 - h_0) + (h_3 - h_0)]/2 \times 10$$

wherein $\rho$ is the density of the NaCl solution in [g/cm³] (1.005 g/cm³ for 0.9% saline solution at 20° C.), and A is the area of the hydrogel layer 28.27 cm², and $\Delta P$ is the hydrostatic pressure 4920 g·cm/s², and the permeability, K, is in units of [cm³ s/g].

The SAP particles, which are surface coated with cationic polymers according to the present invention, preferably have a measured permeability of at least $400 \times 10^{-7}$ cm³ sec/g, more preferably more than $800 \times 10^{-7}$ cm³ sec/g, even more preferably more than $1000 \times 10^{-7}$ cm³ sec/g and most preferably more than $1200 \times 10^{-7}$ cm³ sec/g.

2. Wet Porosity

An important characteristic of SAP particles, which is preferably achieved by the SAP particles according to the present invention, is the openness or porosity of the hydrogel zone or layer formed when the polymer is swollen in body fluids under a confining pressure. This is referred to as Wet Porosity.

The openness or porosity of the hydrogel layer is formed when the SAP particles swell in the presence of body fluids. The Wet Porosity is important to determine the ability of the SAP particles to acquire and transport fluids, especially when the SAP particles are present at high concentrations in the absorbent structure. Porosity refers to the fractional volume that is not occupied by solid material. For a hydrogel layer formed entirely from a SAP, porosity is the fractional volume of the layer that is not occupied by hydrogel. For an absorbent structure containing the hydrogel, as well as other components, porosity is the fractional volume (also referred to as void volume) that is not occupied by the hydrogel, or other solid components (e.g., fibers).

This test determines the porosity of the hydrogel-layer formed by swollen SAP particles in 0.9% saline solution under a confining pressure of 0.3 psi (2.1 kPa). The objective of this test is to assess the ability of the hydrogel-layer formed from SAP particles to remain porous when the SAP particles are present in high concentration in an absorbent layer and exposed to usage mechanical pressure. Wet porosity is the fractional volume of the layer that is not occupied by swollen SAP particles. See J. M. Coulson et al. Chemical Engineering Vol. 2, 3$^{rd}$ Edition, Pergamon Press, 1978, P 126.

Wet porosity of the current invention is measured together with the permeability measurement using the same sample and the sample holder assembly (piston/cylinder apparatus) and additional measurements. In this way, the porosity data can be derived in addition to the closely related permeability values from the same experimental set-up.

Weigh empty sample holder assembly to the accuracy of 0.01 g after the measurement of caliper of empty sample holder (see permeability measurement): $w_0$.

After the drip-off of excess fluid for 30 minutes (as in permeability), weigh sample holder assembly and swollen SAP with fluid in interstitials to the accuracy of 0.01 g: $w_1$.

Dry out the fluid in interstitials by placing the assembly of SAP particles and sample holder on paper hand towels (Metsa Tissue, Katrin®, C-fold2) 16 hours (+/−1 or 2 hrs).

Measure caliper of sample holder assembly and SAP particles after interstitials are dried to the accuracy of 0.01 mm: $h_4$.

Weigh sample holder assembly and SAP particles with dried interstitials to the accuracy of 0.01 g: $w_2$.

The final wet porosity of swollen SAP particles, n, can be obtained as follows:

$$(\text{Wet Porosity}) n = V_{void}/V_{tot}$$

wherein $V_{void}$ is obtained by the weight of liquid in interstitials of the hydrogel-layer obtained from the weight difference between before and after the dry out process with an addition to the weight correction of 0.7 g as below.

$$V_{void} = (w_1 - w_0) - (w_2 - w_0) - 0.7 \text{ (weight correction as fluid clings to sample holder)}/\rho$$

wherein $\rho$ is the density of the NaCl solution in g/cm³ (1.005 g/cm³ for 0.9% saline solution at 20° C.), and $V_{tot}$ is obtained by wet sample caliper and the area of the hydrogel layer A formed from the SAP particles.

$$V_{tot} = (h_3 - h_0/10) \times A$$

The values for $h_0$, $h_3$ and A, are those values, which have been measured in permeability measurement.

In general, the Wet Porosity takes a value between 0 and 1. Preferred SAP particles useful in the present invention have Wet Porosity values of at least 0.20, more preferably at least 0.23, even more preferably at least 0.25. However the porosity remains an important aspect over the whole usage range of pressures experienced by absorbent cores, i.e. starting from no pressure to pressures such as 10 000 Pa.

3. Cylinder Centrifuge Retention Capacity (CCRC)

This test serves to measure the saline-water-solution retention capacity of the SAP particles used herein, when the SAP particles are submitted to centrifuge forces (and it is an indication of the maintenance of the absorption capacity of the SAP particles in use, when also various forces are applied to the material).

First, a saline-water solution is prepared as follows: 18.00 g of sodium chloride is weighed and added into a two liter volumetric flask, which is then filled to volume with 2 liter deionised water under stirring until all sodium chloride is dissolved.

A pan with a minimum 5 cm depth, and large enough to hold four centrifuge cylinders is filled with part of the saline solution, such that up to a level of 40 mm (±3 mm).

Each SAP particles sample is tested in a separate cylinder and each cylinder to be used is thus weighed before any sample is placed in it, with an accuracy of 0.01 g. The cylinders have a very fine mesh on the bottom, to allow fluid to leave the cylinder.

For each measurement, a duplicate test is done at the same time; so two samples are always prepared as follows:

1.00 g of the SAP particles, which are to be tested, is weighed, with an accuracy of 0.005 g (this is the 'sample'), and then the sample is transferred to an empty, weighed cylinder. (This is repeated for the replica.)

Directly after transferring the sample to a cylinder, the filled cylinder is placed into the pan with the saline solution (Cylinders should not be placed against each other or against the wall of the pan.).

After 15 min (±30 s), the cylinder is removed from the pan, and the saline solution is allowed to drain off the cylinder; then, the cylinder is re-placed in the pan for another 45 min. After the total of 60 minutes immersion time, the cylinder is taken from the solution and excess water is allowed to run off the cylinder and then, the cylinder with the sample is placed in the cylinder stands inside a centrifuge, such that the two replicate samples are in opposite positions.

The centrifuge used may be any centrifuge equipped to fit the cylinder and cylinder stand into a centrifuge cup that catches the emerging liquid from the cylinder and capable of delivering a centrifugal acceleration of 250 g (±5 g) applied to a mass placed on the bottom of the cylinder stand (e.g., 1300 rpm for a internal diameter of 264 mm). A suitable centrifuge is Heraeus Megafuge 1.0 VWR # 5211560. The centrifuge is set to obtain a 250 g centrifugal acceleration. For a Heraeus Megafuge 1.0, with a rotor diameter of 264 mm, the setting of the centrifuge is 1300 rpm.

The samples are centrifuged for 3 minutes (±10 s).

The cylinders are removed from the centrifuge and weighed to the nearest 0.01 g.

For each sample (i), the cylinder centrifuge retention capacity $W_i$, expressed as grams of saline-water-solution absorbed per gram of SAP particles is calculated as follows:

$$w_i = \frac{m_{CS} - (m_{Cb} + m_S)}{m_S} \left[\frac{g}{g}\right]$$

wherein:

$m_{CS}$: is the mass of the cylinder with sample after centrifugation [g]

$m_{Cb}$: is the mass of the dry cylinder without sample [g]

$m_S$: is the mass of the sample without saline solution [g]

Then, the average of the two $W_i$ values for the sample and its replica is calculated (to the nearest 0.01 g/g) and this is the CCRC as referred to herein.

Preferably the CCRC of the SAP particles of the present invention is less than 25 g/g, more preferably less than 20 g/g, still more preferably less than 19.5 g/g and most preferably less than 17 g/g. Furthermore, the CCRC of the SAP particles of the present invention is more than 5 g/g, more preferably more than 6 g/g.

4. Free Swell Rate (FSR)

This method serves to determine the swell rate of the SAP particles used herein in a 0.9% saline solution, without stirring or confining pressure. The amount of time taken to absorb a certain amount of fluid is recorded and this is reported in gram of fluid (0.9% saline) absorbed per gram of SAP particles per second, e.g., g/g/sec.

The saline solution is prepared by adding 9.0 gram of NaCl into 1000 ml distilled, deionized water, and this is stirred until all NaCl is dissolved.

The sample amount calculated (see the below equation) is weighed (to an accuracy of 0.0001 g) and placed evenly over the bottom of a 25 ml beaker; then 20 g of the saline solution (also at 23° C.) is added quickly to the beaker with the sample and the timer is started. Exact weight of saline solution added is determined to the accuracy of 0.01 g: $w_{liq}$ $w_{dry}$=dry weight[g]=20 [g]/(0.75×CCRC[g/g])

When the last part of the undisturbed fluid surface meets the swelling sample, e.g., judged by the light reflection from the fluid surface, the time $t_s$ is recorded.

The test is repeated twice, to obtain 3 values.

The Free Swell Rate is then calculated per sample and this can be averaged to obtain the Free Swell Rate, as referred herein.

$FSR = w_{liq}/(w_{dry} \times t_s)$

Preferably, the FSR of the SAP particles of the present invention is at least 0.1 g/g/sec, more preferably at least 0.3 g/g/sec, even more preferably at least 0.5 g/g/sec and most preferably at least 0.7 g/g/sec.

5. Acquisition Test

The fluid acquisition test provides a means for introducing fluid into an absorbent article that simulates in-use conditions. The article will be loaded with a 75 ml/gush of 0.9% Saline solution at a rate of 15 ml s$^{-1}$ using a pump (Model 7520-00 Cole Parmer Instruments Co., Chicago, USA). The time to absorb saline solution is recorded by a timer. The gush is repeated every 5 minutes at precisely 5 minutes gush intervals until 4 gushes.

The test sample, which comprises a core and includes a topsheet and a backsheet, is arranged to lie flat on a foam platform within a perspex box (see the detail assembly of test apparatus in European Patent EP 0 631 768 B1 or U.S. Pat. No. 6,083,210). The core has a ultimate storage capacity of about 300 ml to about 400 ml. If products with significant different capacities should be evaluated (such as can be envisaged for adult incontinence products), the settings in particular of the fluid volume per gush should be adjusted appropriately to about 20% of the total article design capacity, and the deviation from the standard test protocol should be recorded.

The outer surface of the backsheet is facing the foam platform. A Perspex plate having a 5 cm diameter opening substantially in its middle is placed on top of the sample. The sample is oriented such that the topsheet is directly below the opening of the perspex plate. The opening in the plate (=loading point for the saline solution) is placed about 10 cm from the front edge of the complete core and about in the halfway between the lateral sides of the core. Saline solution is introduced to the sample through the cylinder fitted and glued into the opening. Electrodes are about 1 mm to 2 mm above the surface of the absorbent structure and also connected to the timer. Loads are placed on top of the plate to simulate, for example a baby's weight. A weight of 9 kg is placed on top of the plate with an area of 744.6 cm$^2$ (51 cm×14.6 cm).

As saline solution is introduced into the cylinder. It builds up on top of the absorbent structure thereby completing an electrical circuit between the electrodes. This starts the timer. The timer is stopped and recorded when the absorbent structure has absorbed the gush, and the electrical contact between the electrodes is broken.

Acquisition rate is defined as the gush volume absorbed (ml) per unit time (s). The acquisition rate is calculated for each gush introduced into the sample.

Preferred acquisition rates for the $4^{th}$ gush are at least 0.7 ml/s, more preferably at least 0.8 ml/s.

6. Staining of SAP Particles with Toluidine Blue in 0.9% NaCl

With the following method, it is possible to determine, if SAP particles coated with cationic polymers have been surface cross-linked prior to applying the cationic polymer coating on the SAP particles.

Staining Solution (20 ppm Toluidine Blue O in 0.9% NaCl):

20 mg Toluidine Blue O [CAS: 540-23-8] are dissolved in 250 ml 0.9% (w/w) NaCl solution. The mixture is placed into an ultrasonic bath for 1 hour, filtered through a paper filter, and filled up to 1000 ml with 0.9% NaCl solution.

Staining Procedure:

A sample of 30-50 mg of SAP particles coated with cationic polymers is placed into a 40 ml screw cap glass vial, and 30 ml of the above staining solution are added. The vial is closed, and the SAP particles are allowed to swell and equilibrate for 18 hours at 20-25° C. during gentle agitation (e.g., gentle swirling or slow rolling of the vial on a roller mill).

For microscopy assessment, the swollen, stained samples of SAP particles are transferred into white porcelain dishes, and covered with the solution in which they were prepared (or placed into 1 cm glass or quartz cuvettes with a stopper in contact with this solution).

A stereomiscroscope (e.g., Olympus Stereomicroscope SZH10 (7-70×), equipped with a circular illumination (e.g., Intralux UX 6000-1, Volpi AG, CH 8952 Schlieren, Switzland), and optionally a camera (e.g., Olympus ColorView 12), may be used for evaluation of the swollen, stained SAP particles.

As comparative samples, non surface cross-linked SAP particles coated with cationic polymers as well surface cross-linked SAP particles coated with cationic polymers are submitted to the staining method.

Assessment: Surface Cross-Linked Versus Non Surface Cross-Linked SAP Particles:

Swollen and stained non surface cross-linked SAP particles coated with cationic polymers display a uniform, homogeneous staining throughout the individual gel particles and essentially plain surfaces.

Swollen and stained surface cross-linked SAP particles coated with cationic polymers on the other hand show characteristic surface patterns such as flaky surfaces or broken shells. Such pattern cannot be seen in samples of non surface cross-linked SAP particles.

Methods for Making SAP

The basic SAP can be formed in any conventional manner known in the art as discussed above. Typical and preferred processes for producing these polymers are described in a long list of literature including many patent application documents and in particular the textbook "Modern Super Absorbent Technology" by F. L. Buchholz and A. T. Graham, supra, U.S. Reissue Pat. No. 32,649, U.S. Pat. No. 4,666,983, U.S. Pat. No. 4,625,001 U.S. Pat. No. 4,340,706, U.S. Pat. No. 4,506,052 U.S. Pat. No. 4,735,987 U.S. Pat. No. 4,541,871, PCT application WO92/16565, PCT application WO90/08789, PCT application WO93/05080; U.S. Pat. No. 4,824,901; U.S. Pat. No. 4,789,861, U.S. Pat. No. 4,587,30, U.S. Pat. No. 4,734,478; U.S. Pat. No. 5,164,459; German patent application 4,020,780, and published European patent application 509,708.

Preferred methods for forming the basic SAP particles are those involving aqueous solution polymerization methods. The aqueous reaction mixture of monomers is subjected to polymerization conditions, which are sufficient to produce in the mixture, substantially water-insoluble, slightly network cross-linked polymer. The mass of polymer formed can then be pulverized or chopped to form individual particles.

Finally the SAP particles are coated (but not covalently bonded) with the cationic polymers according to the present invention. The cationic polymer can be applied to the SAP particles by simple spraying of a solution comprising the cationic polymer onto the SAP particles in a mixer. Alternatively, a solution containing the cationic polymer can be mixed with SAP particles. Preferably, the cationic polymer is provided in an aqueous solution. Alternatively, the cationic polymer is provided in an organic solution.

Other compounds usual in the art, such as salts for pH buffering or neutralization and dust reducing compounds, or other reaction and process aids can be used in the conventional manner.

When applying the cationic polymer (preferably the N-polymer) to the SAP particles it is important not to bind the coating material covalently to the surface of the SAP particles. It has surprisingly been found, that upon application of the preferred N-polymers according to the present invention, it is neither necessary nor advantageous to bind the cationic polymer to the superabsorbent particles. To ensure this, the temperature of the mixing step are critical characteristics to obtain a coating without bonding, which is sufficiently strong on one hand but effective enough to allow maintaining the wet integrity of absorbent cores made with this SAP. The process step of coating the SAP particles with the cationic polymer is preferably carried out at temperatures below 120° C., more preferably at temperatures below 100° C. A test method to determine, if the cationic polymers are covalently bound to the SAP particles or not is described in U.S. Pat. No. 6,011,196, columns 17 and 18. This test method may be applied on the SAP particles of the present invention.

It is even possible to introduce the cationic polymer into absorbent structures already comprising uncoated SAP particles.

Furthermore, according to the present invention, the cationic polymers are preferably not substantially cross-linked to each other during or after they have been applied on the SAP particles. Therefore, the coating on the SAP particles preferably does not comprise cationic polymers, which are covalently bonded to each other but comprises individual cationic polymers. Hence, the cationic polymers coating the SAP particles according to the present invention are preferably neither covalently bonded to the SAP particle nor are they covalently bonded to each other.

Absorbent Cores Containing SAP Particles

According to the present invention absorbent cores for disposable absorbent articles comprise the previously described SAP particles having a coating of cationic polymers, with or without other optional components such as fibers, thermoplastic material, foams, scrims etc. The principle function of such cores is to absorb the discharged body fluid, and then retain such fluid, even when subjected to pressures and tensions and torsions normally encountered as a result of the wearer's movements of absorbent articles made therewith.

In general, the absorbent cores according to the present invention contain one or more zones. Generally, a high concentration of SAP particles, in accordance with the present invention, is desirable to reduce the level of other components, in particular fibrous components in order to provide relatively thin absorbent articles.

In measuring the concentration of SAP particles in a given zone of an absorbent core, the percent by weight of the SAP particles relative to the combined weight of SAP and any other components (e.g., fibers, thermoplastic material, etc.) that are present in the same zone containing the polymer is used.

The fluid storage zone of the absorbent core may comprise other SAP particles (alone or in addition to the coated SAP particles of the present invention), which do not satisfy the above physical criteria of the SAP particles of the present invention.

The absorbent core or parts thereof (e.g., the fluid acquisition zone or the fluid storage zone or parts of these zones) may in addition be fully or partially wrapped in a tissue, nonwoven or any other suitable substrate in order to unitize the assembly. In one preferred embodiment the core wrap material comprises a top layer and a bottom layer, which layers may be sealed together along their edges, e.g., by adhesive. The top layer and the bottom layer can be provided from a non-woven material. The top layer and the bottom layer may be provided from two or more separate sheets of materials or they may be alternatively provided from a unitary sheet of material. Such a unitary sheet of material may be wrapped around the storage layer, e.g., in a C-fold.

Fluid Acquisition Zone

A key component of diaper of the present invention is the fluid acquisition zone, which comprises the SAP particles of the present invention. This fluid acquisition zone serves to quickly collect and temporarily hold discharged body fluid. A portion of discharged fluid may, depending upon the wearer's position, permeate the acquisition zone and be absorbed by the fluid storage zone in the area proximate to the discharge. However, since fluid is frequently discharged in gushes, the fluid storage zone in such area may not absorb the fluid as quickly as it is discharged. Therefore, the fluid acquisition zone hereof also facilitates transport of the fluid from the point of initial fluid contact to other parts of the absorbent core. In the context of the present invention, it should be noted that the term "fluid" includes, but is not limited to, liquids, urine, menses, perspiration, and water based body fluids.

The fluid handling function of the fluid acquisition zone is of particular importance. The fluid acquisition zone must have sufficient temporary capacity to rapidly absorb a "gush" of a bodily fluid, and sufficient fluid retention to control the acquired fluid under the influence of gravity yet not exhibit excessive fluid retention so as to make it difficult for fluid storage zone to desorb the fluid acquisition zone.

In order to acquire, temporarily hold and transport fluids, the swollen SAP particles have to be especially useful for providing interstices to enable the flow of liquid between the swollen SAP particles. This is in contrast to the common use of most prior art SAP particles which were mainly designed for use in the fluid storage zone and therefore mainly had to be able to absorb and store high amounts of liquid.

The fluid acquisition zone may be comprised of several different materials including but not limited to: a) nonwoven or woven assemblies of synthetic fibers including polyester, polypropylene, or polyethylene, natural fibers including cotton or cellulose, blends of such fibers, or any equivalent materials or combinations of materials and b) compressed regenerated cellulosic sponges. Particularly preferred materials for the fluid acquisition zone are the SAP particles of the present invention. By applying the SAP particles of the present invention, the fluid acquisition remains desirably thin until it is exposed to an aqueous liquid at which time it rapidly expands so as to absorb the liquid.

The fluid acquisition zone is preferably positioned such that it is in fluid communication with topsheet, and serves to quickly acquire and partition body exudates from the wearer's body. Bonding of the fluid acquisition zone the topsheet may enhance the fluid communication by providing interfacial bonding and preventing topsheet separation form impeding fluid flow.

A suitable absorbent core comprises an assembly having (a) at least one fluid acquisition zone comprising relatively high concentrations of SAP particles according to the present invention, preferably at least 50% by weight of the fluid acquisition zone.

In one embodiment, the fluid acquisition zone comprises only one layer. In this embodiment, this layer preferably comprises SAP particles of the present invention in a concentration of at least 50% by weight of this layer, more preferably at least 60% by weight.

In another embodiment, the fluid acquisition zone comprises at least two layers. In this embodiment, at least one of the layers comprises SAP particles of the present invention in a concentration of at least 70% by weight of this at least one layer, more preferably at least 80% by weight.

In a preferred embodiment of the present invention, the fluid acquisition zone comprises an upper acquisition layer facing towards the wearer and a lower acquisition layer. In one preferred embodiment the upper acquisition layer comprises a nonwoven fabric whereas the lower acquisition layer preferably comprises the SAP particles of the present invention. The acquisition layer preferably is in direct or indirect contact with the storage layer.

Preferably, the lower layer comprises SAP particles of the present invention in a concentration of at least 70% by weight of this lower layer, more preferably at least 80% by weight and still more preferably at least 90% by weight.

Absorbent Articles

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis 22 may also include most or all of the absorbent core 28 encased between the topsheet 24 and the backsheet 26. The chassis 22 preferably further includes side panels 30, leg cuffs 32 with elastic members 33 and a waist feature 34. The leg cuffs 32 and the waist feature 34 typically comprise elastic members. One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which, when the diaper is worn, is generally positioned between the wearer's legs.

The waist regions 36 and 38 may include a fastening system comprising fastening members 40 preferably attached to the rear waist region 38 and a landing zone 42 attached to the front waist region 36.

The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

The diaper may also include other features as are known in the art including front and rear ear panels, waist cap features, elastics and the like to provide better fit, containment and aesthetic characteristics.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, absorbent gelling materials, or any other known absorbent material or combinations of materials. The absorbent core may further comprise minor amounts (typically less than 10%) of non-liquid absorbent materials, such as adhesives, waxes, oils and the like. Furthermore, the SAP particles of the present invention can be applied as absorbent materials.

The absorbent cores of the present invention preferably comprise relatively high concentrations of SAP particles. Consequently, there will be little or even no fibrous matrix comprised by the absorbent core, which is able to trap the SAP particles within the fibrous matrix and thus keeping the SAP particles inside the absorbent core. Therefore, the topsheet and the backsheet are preferably joined together (e.g., by adhesive, sewing, needle punching, ultrasonic bonding, by the application of heat and/or pressure or any other method known in the art), at least in those regions, where the SAP particles are most likely to leak out of the absorbent assembly. The respective regions may vary depending on the chosen configuration of the absorbent article.

FIG. 2 shows a cross-sectional view of FIG. 1 taken in the transverse axis 110. In FIG. 2 illustrates a preferred embodiment of the different zones comprised by the absorbent cores. In FIG. 2, the fluid acquisition zone 50 comprises an upper acquisition layer 52 and a lower acquisition layer 54, while the fluid storage zone underneath the fluid acquisition zone comprises a storage layer 60, which is wrapped by an upper core wrap layer 56 and a lower core wrap layer 58.

EXAMPLES

Examples of SAP According to the Present Invention

1. Preparation of a Base Superabsorbent Polymer

To 300 g of glacial acrylic acid (AA), 12.837 g of MethyleneBisAcrylAmide (MBAA) is added and allowed to dissolve at ambient temperature. A 2500 ml resin kettle (equipped with a four-necked glass cover closed with septa, suited for the introduction of a thermometer, syringe needles, and optionally a mechanical stirrer) is charged with this acrylic acid/crosslinker solution. A magnetic stirrer, capable of mixing the whole content, is added. 1166.8 g water are then added (the concentration of AA is 20 w/w-%). Most of the water is added to the resin kettle, and the mixture is stirred until the monomer and water are well mixed. 300 mg of the initiator ("V50" from Waco Chemicals) are dissolved in 20 ml of deionized water. Then, the initiator solution is added together with any remaining water. The resin kettle is closed, and a pressure relief is provided e.g., by puncturing two syringe needles through the septa. The solution is then sparged vigorously with argon via an 80 cm injection needle while stirring at approx. 300 RPM. Stirring is discontinued after approx. 8 minutes, while argon spurging is continued. The solution typically starts to gel after 12-20 minutes total. At this point, persistent bubbles form on the surface of the gel, and the argon injection needle is raised above the surface of the gel. Purging with argon is continued at a lowered flow rate. The temperature is monitored, typically it rises from 20° C. to 60-70° C. within an hour. Once the temperature drops below 60° C., the kettle is transferred into a circulation oven and kept at 60° C. for 15-18 hours.

After this time, the resin kettle is allowed to cool, and the resulting gel is removed into a flat glass dish. The gel is then broken or cut with scissors into small pieces (for example in pieces smaller than 2 mm max. dimension), and transferred into a 6 l glass beaker. 83.26 g of 50% NaOH (the amount of NaOH needed to neutralize 75% of the acid groups of the polymer) is diluted with DI water to 2.5 l, and added quickly to the gel. The gel is stirred until all the liquid is absorbed; then, it is covered and transferred into a 60° C. oven and let equilibrate for 2 days.

After this time, the gel is allowed to cool, then divided up into 2 flat glass dishes, and transferred into a vacuum oven, where it is dried at 100° C./max. vacuum. Once the gel has reached a constant weight (usually 3 days), it is ground using a mechanical mill (e.g., IKA mill) and sieved to obtain SAP particles of the required particle size, e.g., 150 to 850 μm.

The amount of MBAA may be adjusted, depending on what properties are required from the resulting polymers, e.g., when 1.0 mol % (per mol AA) MBAA is used, the resulting SAP particles have a CCRC of about 20 g/g; when 2.0 mol % (per mol AA) MBAA is used, the resulting SAP particles have a CCRC of about 16 g/g; when 5.0 mol % (per mol AA) MBAA is used, the resulting SAP particles have a CCRC of about 8 g/g.

If not otherwise stated, all compounds were obtained from Aldrich Chemicals, Milwaukee, Wis., USA.

2. Surface Cross-Linking Process Step: (Examples I and L Only)

Surface cross-linking of SAP particles is carried out prior to coating. A 150 ml glass beaker is equipped with a mechanical stirrer with a plastic blade, and charged with 100 g of dry SAP particles. The mechanical stirrer is selected in such a way that a good fluidization of the polymers can be obtained at 300-500 RPM. A syringe is charged with a 4% solution (w/w) of EthyleneGlycolDiGlycidylEther (EGDGE) in 1,2-propanediol; another 300 μl syringe is charged with deionised water.

The SAP particles are fluidized in the beaker at approx. 300 RPM, and the surface cross-linking agent (e.g., 100 μl) is added within 30 seconds. Mixing is continued for a total of three minutes. While stirring is continued, 7500 μl of water are then added within 3-5 seconds, and stirring is continued at 300-500 RPM for another 3 minutes. After this time, the beaker is covered with aluminum foil, and let equilibrate for 1 hour. Then the beaker is transferred to a 140° C. oven, and kept at this temperature for 120 minutes. After this time, the material is allowed to cool down, the contents is removed, and the surface cross-linked SAP particles are obtained. Any agglomerates may be carefully broken by gentle mechanical action. The resulting surface cross-linked SAP particles may then be sieved to the desired particle size, e.g., 150-850 µm.

3. Non-Covalently Bonded Surface Coating with a Cationic Polymers

Examples B to D, F to H and K

A 1 l plastic beaker is charged with 50 g of dry SAP particles. The partially hydrolyzed cationic polymer of the hydrolysation levels of 30% (for example B), 50% (for examples C, F, G, H and K) and >90% (for example D), respectively, are added (respectively, Lupamin 9030, Luredur 8097, Lupamin 9095 from BASF) at 0.5 w % (e.g., 2.5 g of coating solution with 10% cationic polymer content) over about 2 minutes while mixing by a conventional cooking mixer at ambient temperature. The adding amount of the cationic polymer are adjusted accordingly to meet different add on levels of 0.1 w % (for example F), 1.0 w % (for example G) and 5.0 w % (for examples B, C, D, H and K), respectively, based on the cationic polymer content of the coating solution. The resulting material is transferred into a glass petri-dish and sticked particles are disassembled. The coated SAP particles are further dried in the oven at 60° C. over night (about 16 hours). Any large agglomerates may be carefully broken. The resulting coated SAP particles may then be sieved to the desired particle size, e.g., 150-850 µm.

Example E

A 1 l plastic beaker is charged with 40 g of dry SAP particles. PEI (polyethyleneimine, MW 750,000 from Aldrich Chemicals, Milwaukee, Wis., USA) is added at 0.4 w % (e.g., 0.78 g of coating solution with 50% cationic polymer content) over about 2 minutes while mixing by a conventional cooking mixer at ambient temperature. The resulting material is transferred into a glass petri-dish and sticked particles are disassembled. The coated SAP particles are further dried in the oven at 60° C. over night (about 16 hours). Any large agglomerates may be carefully broken. The resulting coated SAP particles may then be sieved to the desired particle size, e.g., 150-850 µm.

TABLE 1

Samples
SAP particle size of all samples: 150 µm-850 um

| Sample No: | SAP particles | Cross-linking level [mol %] | Add-on level of coating [w %] | CCRC [g/g] |
|---|---|---|---|---|
| A | Base polymer without coating and without surface cross-linking (comparative Example) | 2.0 | none | 17.0 |
| B | Base polymer with PVFA/PVAm coating 30 mol % hydrolysation degree without surface cross-linking | 2.0 | 0.5 | 16.5 |
| C | Base polymer with PVFA/PVAm coating 50 mol % hydrolysation degree without surface cross-linking | 2.0 | 0.5 | 16.4 |
| D | Base polymer with PVFA/PVAm coating >90 mol % hydrolysation degree without surface cross-linking | 2.0 | 0.5 | 15.9 |
| E | Base polymer with PEI coating without surface cross-linking | 2.0 | 1.0 | 16.8 |
| F | Base polymer with PVFA/PVAm coating 50 mol % hydrolysation degree without surface cross-linking | 2.0 | 0.1 | 16.8 |
| G | Base polymer with PVFA/PVAm coating 50 mol % hydrolysation degree without surface cross-linking | 2.0 | 1.0 | 16.2 |
| H | Base polymer with PVFA/PVAm coating 50 mol % hydrolysation degree without surface cross-linking | 2.0 | 5.0 | 16.4 |
| I | Base polymer without coating; with surface cross-linking (comparative Example) | 2.0 | none | 15.5 |
| J | Base polymer without coating and without surface cross-linking (comparative Example) | 3.8 | none | 10.1 |
| K | Base polymer with PVFA/PVAm coating 50 mol % hydrolysation degree without surface cross-linking | 3.8 | 0.5 | 10.0 |
| L | Base polymer without coating; with surface cross-linking (comparative Example) | 3.8 | none | 9.4 |

PVFA (=N-vinyl-formamide)/PVAm (=polyvinyl-amine):
 Commercial Name: Lupamin and Luredur, respectively, from BASF
 Lupamin 9030 was used for the sample with 30% hydrolysation level (Sample B)
 Lupamin 9095 was used for the sample with >90% hydrolysation level (Sample D)
 Luredur 8097 was used for the samples with 50% hydrolysation level (Samples C, F to H and K)
 Mw 400.000
 Preparation with 10% cationic polymer in solution
PEI (Polyethyleneimine):
 Used for sample E)
 Mw 750.000
 Preparation with 50% cationic polymer in solution All comparative examples are examples of SAP particles, which are not coated with cationic polymers. These comparative examples are not within the scope of the present invention.

TABLE 2

Effects of Coating on Permeability

| Sample No: | Coating | Permeability [$10^{-7}$ cm$^3$sec/g] |
|---|---|---|
| A | Base polymer without coating | 65 |
| B | Base polymer with PVFA/PVAm coating 30 mol % hydrolysation degree | 198 |
| C | Base polymer with PVFA/PVAm coating 50 mol % hydrolysation degree | 1012 |
| D | Base polymer with PVFA/PVAm coating >90 mol % hydrolysation degree | 268 |
| E | Base polymer with PEI coating | 339 |

TABLE 3

Effects of add-on level on permeability

| Sample No: | Add-on level of coating [w %] | Permeability [$10^{-7}$ cm$^3$sec/g] |
|---|---|---|
| A | None | 65 |
| F | 0.1 | 186 |
| C | 0.5 | 1012 |
| G | 1.0 | 1086 |
| H | 5.0 | 405 |

TABLE 4

Effects of Coating on Wet Porosity

| Sample No: | Coating | Add-on level of coating [w %] | Wet Porosity |
|---|---|---|---|
| A | Base polymer without coating | none | 0.206 |
| B | Base polymer with PVFA/PVAm coating 30 mol % hydrolysation degree | 0.5 | 0.285 |
| C | Base polymer with PVFA/PVAm coating 50 mol % hydrolysation degree | 0.5 | 0.339 |
| D | Base polymer with PVFA/PVAm coating >90 mol % hydrolysation degree | 0.5 | 0.306 |
| E | Base polymer with PEI coating | 1.0 | 0.297 |
| F | Base polymer with PVFA/PVAm coating 50 mol % hydrolysation degree | 0.1 | 0.247 |
| G | Base polymer with PVFA/PVAm coating 50 mol % hydrolysation degree | 1.0 | 0.318 |
| H | Base polymer with PVFA/PVAm coating 50 mol % hydrolysation degree | 5.0 | 0.245 |

TABLE 5

Effects of surface cross-linking versus cationic polymer coating on permeability

| Sample No: | Cross-linking level [mol %] | Surface-cross-linking | Coating | permeability [$10^{-7}$ cm$^3$sec/g] |
|---|---|---|---|---|
| A | 2.0 | no | No | 65 |
| C | 2.0 | no | Yes | 1012 |
| I | 2.0 | yes | no | 306 |
| J | 3.8 | no | no | 109 |
| K | 3.8 | no | yes | 1426 |
| L | 3.8 | yes | no | 263 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a substantially liquid pervious topsheet, a substantially liquid impervious backsheet and an absorbent core between said topsheet and said backsheet, wherein said topsheet and said backsheet are at least partially joined together, and wherein said absorbent core comprises a storage zone and a fluid acquisition zone discrete from and adjacent to said storage zone, wherein said fluid acquisition zone comprises surface-coated superabsorbent polymer particles, wherein:
   a) said surface-coated superabsorbent polymer particles comprise superabsorbent polymer particles having a surface, and cationic polymers on the surface of the superabsorbent polymer particles, wherein said cationic polymers have 1 to 25 mol/kg, referring to the total weight of the cationic polymers, of cationic groups, which can be protonated, wherein said cationic polymers are not substantially covalently bound to said superabsorbent polymer particles; and
   b) said surface-coated superabsorbent polymer particles of the fluid acquisition zone have a Cylinder Centrifuge Retention Capacity (CCRC) of less than 20 g/g;
   further wherein the storage zone does not comprise superabsorbent polymer particles which have a CCRC of less than 25 g/g; wherein said fluid acquisition zone comprises said surface-coated superabsorbent polymer particles in a concentration of at least 50% by weight of said fluid acquisition zone; and
   said superabsorbent polymer particles of the fluid acquisition zone are substantially free of covalent surface cross-links.

2. Absorbent article according to claim 1, wherein said fluid acquisition zone comprises at least one layer and wherein said surface-coated superabsorbent particles are comprised by said at least one layer in a concentration of at least 70% by weight of said acquisition layer.

3. Absorbent article according to claim 1, wherein said superabsorbent polymer particles of the fluid acquisition zone are slightly network cross-linked to each other.

4. Absorbent article according to claim 1, wherein said cationic polymers are nitrogen-containing cationic polymers.

5. Absorbent article according to claim 4, wherein said nitrogen-containing cationic polymers are partially hydrolyzed.

6. Absorbent article according to claim 5, wherein said nitrogen-containing cationic polymers are hydrolyzed in the range of 30% to 80%.

7. Absorbent article according to claim 1, wherein said cationic polymers are primary amines, secondary amines or tertiary amines.

8. Absorbent article according to claim 1, wherein said surface-coated superabsorbent polymer particles of the fluid acquisition zone have a permeability of at least 400×$10^{-7}$ cm$^3$ sec/g.

9. Absorbent article according to claim 1, wherein said surface-coated superabsorbent polymer particles of the fluid acquisition zone have a Wet Porosity of at least 0.20.

* * * * *